(12) United States Patent
Coquerel et al.

(10) Patent No.: US 7,645,905 B2
(45) Date of Patent: Jan. 12, 2010

(54) CRYSTALLINE FORM IV OF AGOMELATINE, A PROCESS FOR ITS PREPARATION AND PHARMACEUTICAL COMPOSITIONS CONTAINING IT

(75) Inventors: Gerard Coquerel, Boos (FR); Julie Linol, Rouen (FR); Jean-Claude Souvie, Le Havre (FR)

(73) Assignee: Les Laboratoires Servier, Suresnes Cedex (FR)

( * ) Notice: Subject to any disclaimer, the term of this patent is extended or adjusted under 35 U.S.C. 154(b) by 68 days.

(21) Appl. No.: 11/497,696

(22) Filed: Aug. 2, 2006

(65) Prior Publication Data

US 2006/0270875 A1 Nov. 30, 2006

Related U.S. Application Data

(60) Provisional application No. 60/704,984, filed on Aug. 3, 2005.

(30) Foreign Application Priority Data

Aug. 3, 2005 (FR) .................................. 05 08277

(51) Int. Cl.
*C07C 233/64* (2006.01)
(52) U.S. Cl. ........................ 564/172; 564/219; 514/617
(58) Field of Classification Search ................ 564/172, 564/219; 514/617
See application file for complete search history.

(56) References Cited

U.S. PATENT DOCUMENTS

2005/0164987 A1* 7/2005 Barberich .................... 514/58

FOREIGN PATENT DOCUMENTS

| EP | 0447285 | 9/1991 |
|----|---------|--------|
| EP | 1564202 | 8/2005 |

OTHER PUBLICATIONS

B.Tinant et al Acta Cryst. 1994, C50, 907-910.*
J.Haleblian, W.McCrone, Pharmaceutical Applications of Polymorphism Journal of Pharmaceutical Science, Aug. 1969, vol. 58(8) pp. 911-929.*
S.R.Byrn, R.R.Pfeiffer, J.G.Stowell, Solid-state chemistry of drugs, 1999, pp. 62-63.*
A.M.Rouhi, The right stuff, Chemical & Engineering News, Feb. 24, 2004, pp. 32-34.*
H.G.Brittain, E.F.Fiese, Effects of pharmaceutical processing on drug polymorphs and solvates, Polymorphism in Pharmaceuticals Solids, 1999, pp. 331-361.*
Tinant, B. et al., "N-[2-(7-methoxy-1-naphthyl)ethyl]acetamid E, a potent melatonin analog" ACTA Crystallographic section C. Crystal structure communications, vol. C50, No. 6, p. 907-910, 1994.
Depreux, P., et al., "Synthesis and structure-activity relationship of novel naphthalenic and bioisosteric amidic derivatives as melatonin receptor ligands" Journal of Medicinal Chemistry, vol. 37, No. 20, p. 3231-3239, 1994.
Chilman-Blair, K., et al., "Agomelatine antidepressant treatment of bipolar disorder melatonin agonist/5-HT20 antagonist" Durgs of the Future, vol. 28, No. 1, p. 7-13, 2003.
Preliminary Search Report for FR 0508277 of Jun. 26, 2006.

* cited by examiner

*Primary Examiner*—Daniel M Sullivan
*Assistant Examiner*—Sudhakar Katakam
(74) *Attorney, Agent, or Firm*—Hueschen and Sage

(57) ABSTRACT

Crystalline form IV of the compound of formula (I):

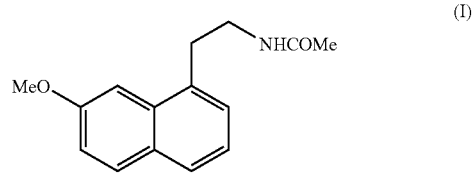

characterised by its powder X-ray diffraction diagram.

Medicinal products containing the same which are useful in the treatment of melatoninergic disorders.

3 Claims, No Drawings

CRYSTALLINE FORM IV OF AGOMELATINE, A PROCESS FOR ITS PREPARATION AND PHARMACEUTICAL COMPOSITIONS CONTAINING IT

The present invention relates to a new crystalline form IV of agomelatine, or N-[2-(7-methoxy-1-naphthyl)ethyl]acetamide, of formula (I):

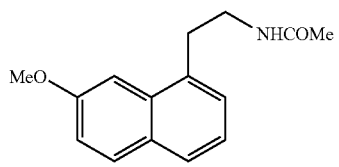

a process for its preparation and pharmaceutical compositions containing it.

BACKGROUND OF THE INVENTION

Agomelatine, or N-[2-(7-methoxy-1-naphthyl)ethyl]acetamide, has valuable pharmaco-logical properties.

Indeed it has the double feature of being, on the one hand, an agonist of melatoninergic system receptors and, on the other hand, an antagonist of the $5\text{-}HT_{2c}$ receptor. Those properties confer activity in the central nervous system and, more especially, in the treatment of severe depression, seasonal affective disorders, sleep disorders, cardiovascular pathologies, pathologies of the digestive system, insomnia and fatigue resulting from jetlag, appetite disorders and obesity.

DESCRIPTION OF THE PRIOR ART

Agomelatine, its preparation and its therapeutic use have been described in European Patent Specification EP 0 447 285.

In view of the pharmaceutical value of this compound, it has been important to be able to obtain it with excellent purity, with well defined crystalline form, perfectly reproducible, which as a result exhibits valuable characteristics in terms of formulation and sufficiently stable to allow its storage for long periods without particular requirements for temperature, light, humidity or oxygen level.

Patent Specification EP 0 447 285 describes the preparation of agomelatine in eight steps, starting from 7-methoxy-1-tetralone. However, that document does not specify the conditions for obtaining agomelatine in a form that exhibits those characteristics in a reproducible manner.

DETAILED DESCRIPTION OF THE INVENTION

The Applicant has now developed a new synthesis process that allows agomelatine to be obtained in a well defined, perfectly reproducible crystalline form that especially exhibits valuable characteristics for formulation.

More specifically, the present invention relates to the crystalline form IV of the compound of formula (I), characterised by the following powder X-ray diffraction diagram, measured using a Siemens D5005 diffractometer (copper anticathode) and expressed in terms of inter-planar distance d, Bragg's angle 2 theta, intensity and relative intensity (expressed as a percentage of the most intense ray):

| 2-Theta (°) exp. | d (Å) exp. | Intensité (%) |
|---|---|---|
| 5.04 | 17.524 | 8 |
| 10.16 | 8.703 | 68 |
| 10.51 | 8.409 | 9 |
| 15.22 | 5.818 | 28 |
| 16.75 | 5.288 | 39 |
| 17.41 | 5.089 | 60 |
| 18.03 | 4.915 | 100 |
| 18.81 | 4.714 | 71 |
| 20.48 | 4.333 | 37 |
| 21.61 | 4.110 | 16 |
| 23.27 | 3.819 | 11 |
| 24.04 | 3.699 | 26 |
| 24.27 | 3.665 | 42 |
| 24.77 | 3.591 | 24 |
| 25.57 | 3.481 | 13 |
| 27.06 | 3.292 | 6 |
| 27.95 | 3.190 | 11 |

The invention relates also to a process for the preparation of the crystalline form IV of the compound of formula (I), which process is characterised in that agomelatine is heated at 110° C. until the melting be completed, and is then rapidly cooled between 50 and 70° C., and maintained for about 5 hours at 70° C. until crystallisation.

An advantage of obtaining that crystalline form is that it allows the preparation of pharmaceutical formulations having a consistent and reproducible composition, which is especially advantageous when the formulations are to be used for oral administration.

A pharmacological study of the form IV so obtained has demonstrated that it has substantial activity in respect of the central nervous system and in respect of microcirculation, enabling it to be established that the crystalline form IV of agomelatine is useful in the treatment of stress, sleep disorders, anxiety, severe depression, seasonal affective disorders, cardiovascular pathologies, pathologies of the digestive system, insomnia and fatigue due to jetlag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the crystalline IV form of agomelatine can be used in the treatment of sexual dysfunction, that it has ovulation-inhibiting and immunomodulating properties and that it lends itself to use in the treatment of cancers.

The crystalline form IV of agomelatine will preferably be used in the treatment of severe depression, seasonal affective disorders, sleep disorders, cardiovascular pathologies, insomnia and fatigue due to jetlag, appetite disorders and obesity.

The invention relates also to pharmaceutical compositions comprising as active ingredient the crystalline form IV of agomelatine together with one or more appropriate inert, non-toxic excipients. Among the pharmaceutical compositions according to the invention there may be mentioned, more especially, those which are suitable for oral, parenteral (intravenous or subcutaneous) or nasal administration, tablets or dragées, granules, sublingual tablets, gelatin capsules, lozenges, suppositories, creams, ointments, dermal gels, injectable preparations, drinkable suspensions and disintegrable pastes.

The useful dosage can be adapted according to the nature and the severity of the disorder, the administration route and the age and weight of the patient. The dosage varies from 0.1 mg to 1 g per day in one or more administrations.

The Examples below illustrate the invention but do not limit it in any way.

EXAMPLE 1

Crystalline form IV of
N-[2-(7-Methoxy-1-naphthyl)ethyl]acetamide 100 g of N-[2-(7-Methoxy-1-naphthyl)ethyl]acetamide are heated at 110° C. until the melting be completed, and is then rapidly cooled between 50 and 70° C., and maintained for 5 hours at 70° C. until crystallisation. The crystalline form IV obtained is characterised by the following powder X-ray diffraction diagram, measured using a Siemens D5005 diffractometer (copper anticathode) and expressed in terms of inter-planar distance d, Bragg's angle 2 theta, intensity and relative intensity (expressed as a percentage of the most intense ray):

| 2-Theta (°) exp. | d (Å) exp. | Intensité (%) |
|---|---|---|
| 5.04 | 17.524 | 8 |
| 10.16 | 8.703 | 68 |
| 10.51 | 8.409 | 9 |
| 15.22 | 5.818 | 28 |
| 16.75 | 5.288 | 39 |
| 17.41 | 5.089 | 60 |
| 18.03 | 4.915 | 100 |
| 18.81 | 4.714 | 71 |
| 20.48 | 4.333 | 37 |
| 21.61 | 4.110 | 16 |
| 23.27 | 3.819 | 11 |
| 24.04 | 3.699 | 26 |
| 24.27 | 3.665 | 42 |
| 24.77 | 3.591 | 24 |
| 25.57 | 3.481 | 13 |
| 27.06 | 3.292 | 6 |
| 27.95 | 3.190 | 11 |

EXAMPLE 2

Pharmaceutical Composition

| Compound of Example 1 | 25 g |
|---|---|
| Lactose monohydrate | 62 g |
| Magnesium stearate | 1.3 g |
| Maize starch | 26 g |
| Maltodextrines | 9 g |
| Silica, colloidal anhydrous | 0.3 g |
| Sodium starch glycolate type A | 4 g |
| Stearic acid | 2.6 g |

Formulation for the preparation of 1000 tablets each containing a dose of 25 mg:

EXAMPLE 3

Pharmaceutical Composition

Formulation for the preparation of 1000 tablets each containing a dose of 25 mg:

| Compound of Example 1 | 25 g |
|---|---|
| Lactose monohydrate | 62 g |
| Magnesium stearate | 1.3 g |
| Povidone | 9 g |
| Silica, colloidal anhydrous | 0.3 g |
| Sodium cellulose glycolate | 30 g |
| Stearic acid | 2.6 g |

We claim:

1. A crystalline form IV of the compound of formula (I):

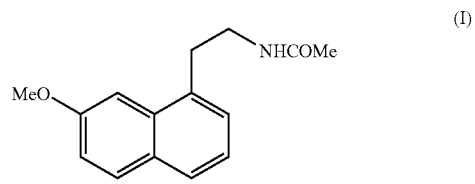

wherein the compound exhibits the following powder X-ray diffraction diagram, measured using a diffractometer (copper anticathode) and expressed in terms of inter-planar distance d (expressed in Å), Bragg's angle 2 theta (expressed in degrees), intensity and relative intensity (expressed as a percentage with respect to the most intense ray):

| 2-Theta (°) exp. | d (Å) exp. | Intensité (%) |
|---|---|---|
| 5.04 | 17.524 | 8 |
| 10.16 | 8.703 | 68 |
| 10.51 | 8.409 | 9 |
| 15.22 | 5.818 | 28 |
| 16.75 | 5.288 | 39 |
| 17.41 | 5.089 | 60 |
| 18.03 | 4.915 | 100 |
| 18.81 | 4.714 | 71 |
| 20.48 | 4.333 | 37 |
| 21.61 | 4.110 | 16 |
| 23.27 | 3.819 | 11 |
| 24.04 | 3.699 | 26 |
| 24.27 | 3.665 | 42 |
| 24.77 | 3.591 | 24 |
| 25.57 | 3.481 | 13 |
| 27.06 | 3.292 | 6 |
| 27.95 | 3.190 | 11. |

2. A process for the preparation of the crystalline form IV of the compound of formula (I) of claim 1, wherein agomelatine is heated at 110° C. until completely melted, is then rapidly cooled between 50 and 70° C., and is maintained for about 5 hours at 70° C. until crystallisation occurs.

3. A pharmaceutical solid composition comprising as active ingredient an effective amount of crystalline form IV of the compound of claim 1, in combination with one or more pharmaceutically acceptable, inert, non-toxic carriers.

* * * * *